United States Patent
Han et al.

(10) Patent No.: US 9,692,397 B2
(45) Date of Patent: Jun. 27, 2017

(54) CARBON BASED CMOS SENSOR RING OSCILLATOR

(71) Applicant: International Business Machines Corporation, Armonk, NY (US)

(72) Inventors: Shu-Jen Han, Cortlandt Manor, NY (US); Keith A. Jenkins, Sleepy Hollow, NY (US)

(73) Assignee: International Business Machines Corporation, Armonk, NY (US)

( * ) Notice: Subject to any disclaimer, the term of this patent is extended or adjusted under 35 U.S.C. 154(b) by 25 days.

(21) Appl. No.: 14/753,060

(22) Filed: Jun. 29, 2015

(65) Prior Publication Data
US 2016/0377566 A1    Dec. 29, 2016

(51) Int. Cl.
*G01N 27/04* (2006.01)
*H03K 3/03* (2006.01)
*G01N 27/414* (2006.01)

(52) U.S. Cl.
CPC ....... *H03K 3/0315* (2013.01); *G01N 27/4148* (2013.01)

(58) Field of Classification Search
CPC . H03K 3/03; H03K 3/354; H03L 5/02; H03L 1/02; H04N 5/369; H04N 5/376; G01R 23/00; G01K 7/00
USPC ......................................................... 702/75
See application file for complete search history.

(56) References Cited

U.S. PATENT DOCUMENTS

| | | | |
|---|---|---|---|
| 5,895,629 A | 4/1999 | Russell et al. | |
| 6,184,754 B1 * | 2/2001 | Kaneko | H03K 3/354 327/159 |
| 6,902,701 B1 | 6/2005 | Hughes et al. | |
| 8,105,538 B2 | 1/2012 | Ramamurthy et al. | |
| 8,312,759 B2 | 11/2012 | McAlister | |
| 8,479,558 B2 | 7/2013 | Dimmler et al. | |
| 8,512,533 B2 | 8/2013 | Wang et al. | |
| 9,083,352 B2 * | 7/2015 | Hirata | |
| 2005/0221473 A1 | 10/2005 | Dubin et al. | |
| 2007/0029612 A1 * | 2/2007 | Sandhu | B82Y 10/00 257/347 |

(Continued)

FOREIGN PATENT DOCUMENTS

| EP | 0908725 A1 | 4/1999 |
|---|---|---|
| EP | 0908725 B1 | 5/2004 |

(Continued)

OTHER PUBLICATIONS

Heves et al., "A novel single-chip RF-voltage-controlled oscillator for bio-sensing applications", Proceedings of the Eurosensors XXIII conference, ScienceDirect, Procedia Chemistry vol. 1, (2009) pp. 1007-1010, Elsevier.

(Continued)

*Primary Examiner* — Jermele M Hollington
*Assistant Examiner* — Zannatul Ferdous
(74) *Attorney, Agent, or Firm* — Michael O'Keefe

(57) ABSTRACT

A structure is provided for sensing an analyte in an environment. The structure may include a ring oscillator on a semiconductor substrate, the ring oscillator includes an AND gate, an odd number of inverters, and a carbon device connected in series, the carbon device is exposed to an environment such that a frequency of the ring oscillator changes when the carbon device is exposed to the analyte in the environment.

17 Claims, 7 Drawing Sheets

(56) References Cited

U.S. PATENT DOCUMENTS

| | | | |
|---|---|---|---|
| 2007/0139031 A1* | 6/2007 | Park | G06F 17/5036 324/76.11 |
| 2009/0096495 A1* | 4/2009 | Keigo | G01K 7/01 327/142 |
| 2012/0261274 A1* | 10/2012 | Rearick | G01N 27/27 205/789 |
| 2013/0237455 A1 | 9/2013 | Dimmler et al. | |
| 2013/0328016 A1 | 12/2013 | Guo et al. | |

FOREIGN PATENT DOCUMENTS

| | | |
|---|---|---|
| EP | 1474697 B1 | 7/2007 |
| JP | 2014009955 A | 1/2014 |
| WO | 03069360 A1 | 8/2003 |
| WO | 2013144340 A1 | 10/2013 |

OTHER PUBLICATIONS

Lei et al., "Simple graphene chemiresistors as pH sensors: fabrication and characterization", Measurement Science and Technology, 2011, vol. 22, No. 10, pp. 1-23.

Han et al., "Graphene radio frequency receiver integrated circuit", nature Communications, Article, Published Jan. 30, 2014, pp. 1-6, www.nature.com/articles/ncomms4086.

Livi et al., "A Hybrid FinFET-based Biosensor with Integrated Readout Capability", Proc. Eurosensors XXVI, Sep. 9-12, 2012, Kraków, Poland, Procedia Engineering vol. 47 (2012) pp. 821-824, SciVerse ScienceDirect, Elsevier.

Ulintz, "Hole Extrusions—Part 1", MetalForming Magazine Xtra, Tooling by Design, Oct. 1, 2011, http://www.metalformingmagazine.com/magazine/article.asp?iid=69 &aid=6177, pp. 1-3.

MetalForming Magazine Xtra, "Hole Extrusions—Part 2", Tooling by Design, Nov. 1, 2011, http://www.metalformingmagazine.com/magazine/article.asp?iid=70&aid=6314, pp. 1-2.

Ulintz, "Hole Extrusions—Part 3", MetalForming Magazine Xtra, Tooling by Design, Dec. 1, 2011, http://www.metalformingmagazine.com/magazine/article.asp?iid=71 &aid=6410, pp. 1-2.

Park et al., "High-density integration of carbon nanotubes via chemical self-assembly", Nature Nanotechnology, Advance Online Publication, www.nature.com/naturenanotechnology, Published Online Oct. 28, 2012, DOI: 10.1038/NNANO.2012.189, pp. 1-5.

* cited by examiner

CARBON BASED CMOS SENSOR RING OSCILLATOR

BACKGROUND

The present invention generally relates to a carbon based environmental sensor, and more particularly to a carbon based digital sensor fabricated on silicon.

Sensing of chemical and biological elements in the environment is important for environmental monitoring and security concerns. It is desirable to have sensors with high sensitivity to such elements, and also to transmit the sensed information remotely, by wired or wireless means, to a distant monitoring point.

Graphene, which is a two-dimensional crystal of carbon atoms, can be used for gas and chemical sensing or biosensing. Carbon nanotubes are a rolled up crystals of carbon, with a crystal structure the same as graphene. Due to their large surface-to-volume ratio and electronic sensitivity to surface molecules, graphene and carbon nanotubes can be used for sensing an analyte, such as an environment gas or chemical. The electronic sensitivity of graphene and carbon nanotubes can be manifested as a change in their resistance when molecules are absorbed from the environment. Graphene can be treated, functionalized, or carbon engineered to detect specific molecules or analytes. Graphene and carbon nanotubes can be used for sensing analytes and to provide a digital signal. An analyte can also be referred to as a reactant.

SUMMARY

According to one embodiment of the present invention, a method of forming a sensor is provided. The sensor may include forming a ring oscillator on a semiconductor substrate, the ring oscillator includes an AND gate, an odd number of inverters, and a carbon device connected in series.

According to another embodiment, a structure is provided. The structure may include a ring oscillator on a semiconductor substrate, the ring oscillator includes an AND gate, an odd number of inverters, and a carbon device connected in series, the carbon device is exposed to an environment such that a frequency of the ring oscillator changes when the carbon device is exposed to an analyte in the environment. A carbon device may include at least one of carbon nanotubes or graphene.

According to another embodiment, a method of sensing an analyte in an environment is provided. The method may include measuring a frequency of a ring oscillator on a semiconductor substrate, where the ring oscillator includes an AND gate, an odd number of inverters, and a carbon device connected in series, where the frequency of the ring oscillator changes when the carbon device is exposed to the analyte in the environment.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
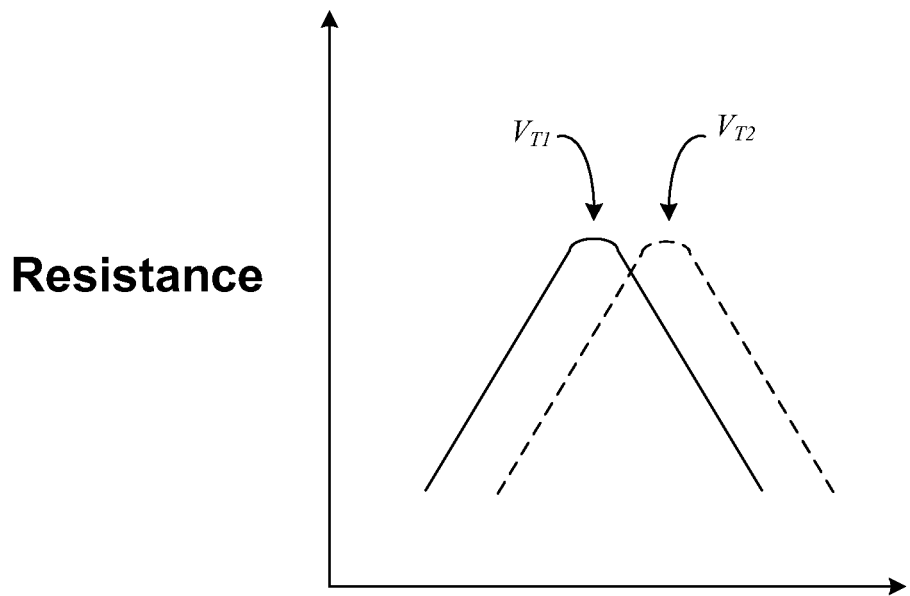
FIG. 1 is a graph according to an exemplary embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed structures and methods, as oriented in the drawing figures. The terms "overlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

Environmental sensors are useful to monitor air quality and can be used for leak detection and monitoring hazardous pollutants. This can help protect the environment and human health. A wireless digital sensor can send information electronically from one location to another location. The information can be stored for comparison between two locations and over a period of time for the same location.

One method of fabricating environmental sensors is described in detail below by referring to the accompanying drawings in FIGS. 1 to 9, in accordance with an illustrative embodiment. In the present embodiment, a semiconductor ring oscillator which incorporates carbon nanotubes or graphene is used as an environmental sensor.

Referring now to FIG. 1, a graph 100 according to an exemplary embodiment is shown. Graph 100 shows a carbon field effect transistor (hereinafter "FET") property of a resistance as a function of a gate voltage. As shown in the graph 100, as a FET gate voltage (hereinafter "gate voltage") increases, the resistance increases until the resistance reaches a maximum resistance. The maximum resistance occurs when the gate voltage reaches a threshold voltage, $V_{T1}$. When the gate voltage continues to increase beyond the threshold voltage, the resistance decreases. The solid line in the graph 100 shows a normal operating condition of resistance vs gate voltage of an FET fabricated with a graphene or carbon nanotube gate channel, while the dashed line in the graph 100 depicts a shift of the resistance-voltage characteristic curve when influenced by the presence of a chemical molecule or an analyte. In an embodiment, the FET channel may include graphene or carbon nanotubes and the absorption of the analyte on the graphene or carbon nanotubes may influence the channel resistance vs gate voltage of the FET. As shown in graph 100, $V_{T1}$ is the threshold voltage for a graphene FET before the chemical module or the analyte is present and $V_{T2}$ is the threshold voltage for an FET with the chemical molecule attached or with the analyte present.

The graphene or carbon nanotubes can affect an electrical characteristic as demonstrated in FIG. 1. Surface functionalization can be done to the graphene or carbon nanotubes, such that they are sensitized to absorb a specific analyte. The presence of a specific analyte will affect a resistance property of the graphene or carbon nanotube. In this manner, the graphene or carbon nanotubes can be used as environmental sensors. The resistance property will be different in the graphene or carbon nanotubes depending on the presence or absence of the specific analyte. In an embodiment, graphene or carbon nanotubes can be made as a resistor.

Graphene or carbon nanotubes can be treated, functionalized, or carbon engineered to detect specific molecules or analytes. In an embodiment, a resistor which includes graphene or carbon nanotubes can be used as an environmental sensor. The resistor may have different resistive properties when it is exposed to the analyte versus when the resistor is not exposed to the analyte. In another embodiment, a FET may include a graphene channel. The FET may have a different voltage threshold when it is exposed to the analyte versus when the FET is not exposed to the analyte.

In an embodiment, an analyte may be an acidic gas, such as Hydrogen Chloride (HCl), pH value, glucose, carbon monoxide or explosive gases.

Figure 2:
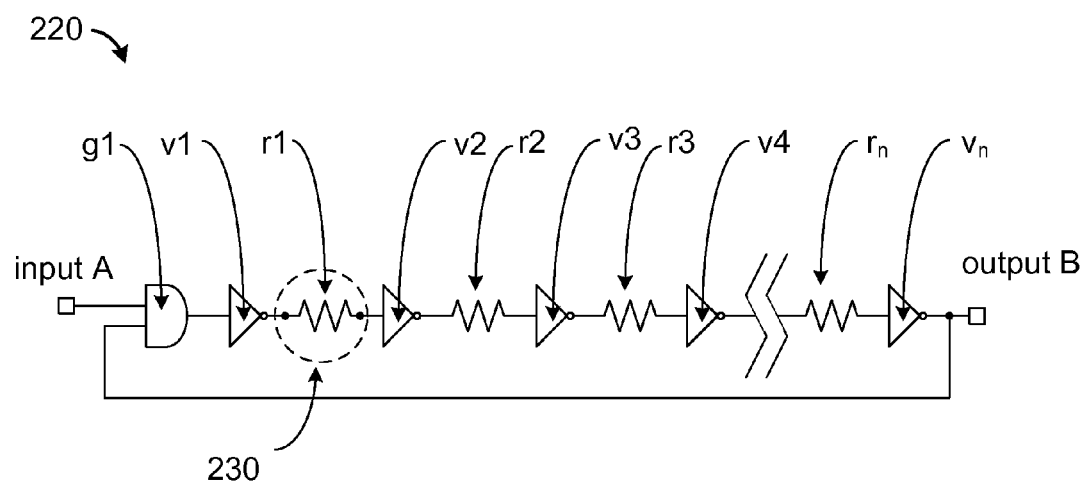
FIG. 2 is an electrical circuit diagram of an oscillator according to an exemplary embodiment.

Referring now to FIG. 2, an electrical circuit of an embodiment of a ring oscillator 220 is shown, according to an exemplary embodiment. The ring oscillator 220 includes an input A, an output B, an AND gate g1, inverters v1, v2, v3, v, . . . $v_n$, and resistors r1, r2, r3, . . . $r_n$. The inverters v1, v2, v3, v4, . . . $v_n$ are connected in series, and the resistors r1, r2, r3, . . . $r_n$ are electrically connected between the inverters v1, v2, v3, v4, . . . $v_n$. The AND gate g1 has inputs of the input A and an output of the last inverter in the series, inverter $v_n$. The output of the last inverter $v_n$ is also output B. The resistors r1, r2, r3, . . . $r_n$ may include graphene or carbon nanotubes.

Following is a description of the operation of the ring oscillator 220. The ring oscillator 220 is an electrical circuit which is includes an odd number of semiconductor inverters v1-$v_n$. An output of each inverter oscillates between a voltage high level and a voltage low level. The inverters v1-$v_n$ are connected in series with an output of a last inverter, inverter $v_n$, connected to an input of the AND gate g1. The AND gate g1 combines the output of the last inverter with the input A to the ring oscillator. The output of the last inverter, inverter $v_n$, is the output B of the ring oscillator. The feedback of the output of the last inverter into the AND gate g1 and subsequently into the inverter v1 causes a voltage level oscillation at the output B. A ring oscillator period is twice the sum of the delay through each of the inverters v1-$v_n$. The ring oscillator period is a duration time of one cycle in a repeating event. An oscillator frequency is a reciprocal of the oscillator period. The input A can turn the oscillation on or off.

An addition of an additional electronic element in a ring oscillator, will affect the oscillator frequency. In an embodiment, resistors r1-$r_n$ have been added to the ring oscillator 220. In an embodiment, resistors r1-$r_n$ may include graphene or carbon nanotubes. Furthermore, the graphene or carbon nanotubes may have a different resistance based on a detection of a specific analyte, as described above. When a resistance is present between the stages, the frequency of oscillation is less than an ordinary ring oscillator by an amount approximately equal to 1/(RC) where R is the resistance of the sensing element and C is the input capacitance of the inverter. Hence if the resistance changes due to an analyte on the graphene or carbon nanotube, the frequency of the oscillator will change accordingly.

In an embodiment, the ring oscillator 220 may be used as an environmental sensor of a specific analyte, such that the frequency of the ring oscillator 220 may change in the presence of an analyte.

It should be noted that, while the embodiment depicted in the figures includes one AND gate g1, five inverters v1-$v_n$ and four resistors r1-$r_n$, any number of resistors and an odd number of inverters may be used.

Figure 3:
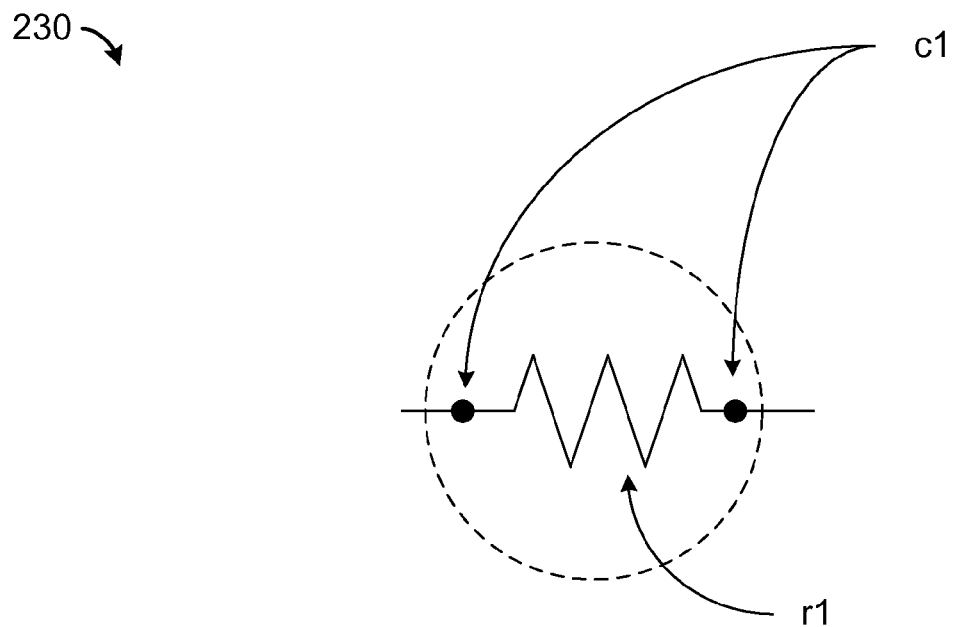
FIG. 3 is an electrical circuit diagram of a resistor according to an exemplary embodiment.
Figure 4:
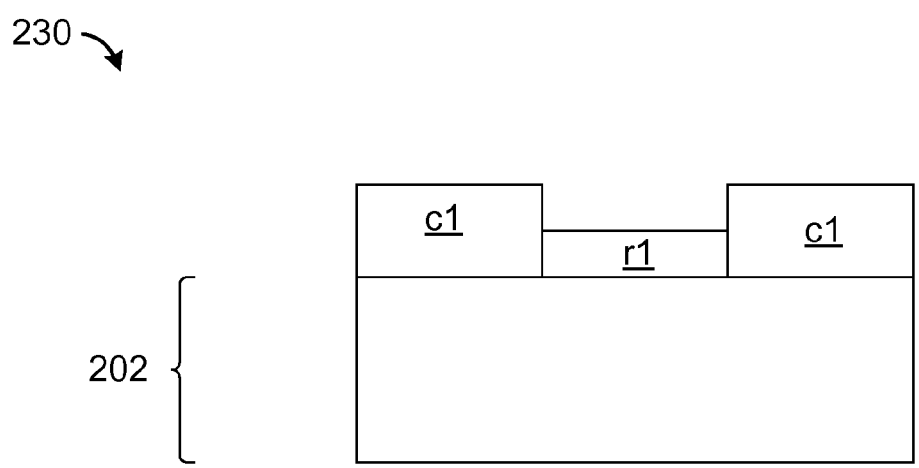
FIG. 4 is a cross-sectional view of a semiconductor structure according to an exemplary embodiment.

Referring now to FIGS. 3 and 4, FIG. 3 is an embodiment of an electrical circuit diagram of the resistor r1, while FIG. 4 is an embodiment of a semiconductor cross sectional view of the resistor r1. FIG. 3 is a sectional view 230 of FIG. 5. The resistor r1 may include a contact c1. The resistor r1 may be fabricated on a first base substrate 202. In an embodiment, the resistor r1 includes graphene or carbon nanotubes.

The first base substrate 202 may be made from any of several known semiconductor materials such as, for example, a bulk silicon substrate. Other non-limiting examples include silicon, germanium, silicon-germanium alloy, silicon carbide, silicon-germanium carbide alloy, and compound (e.g. III-V and II-VI) semiconductor materials. Non-limiting examples of compound semiconductor materials include gallium arsenide, indium arsenide, and indium phosphide. Typically the first base substrate 202 may be approximately, but is not limited to, several hundred microns thick. For example, the first base substrate 202 may include a thickness ranging from 0.5 mm to about 1.5 mm.

Figure 5:
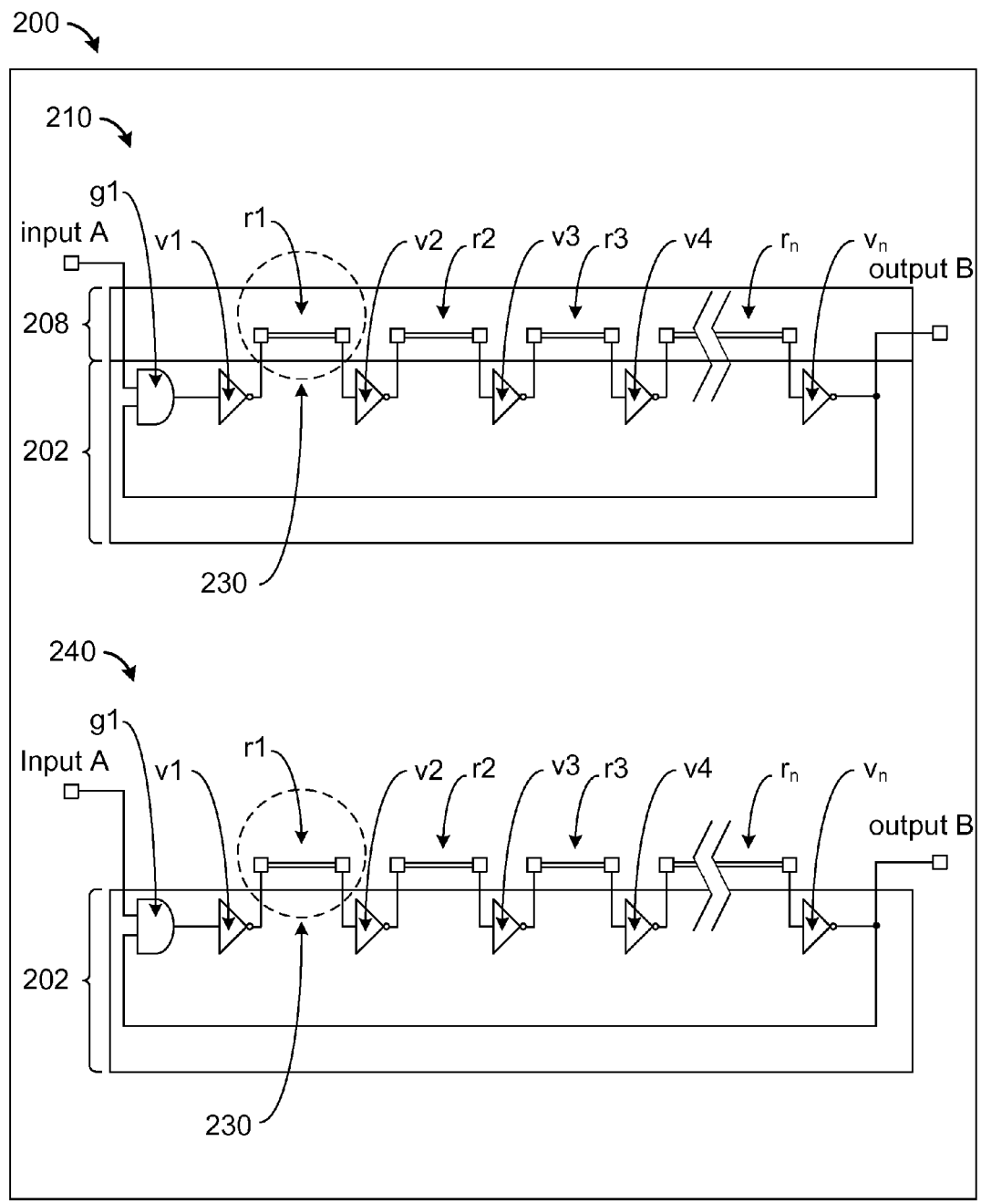
FIG. 5 is a view of a sensor according to an exemplary embodiment.

Referring now to FIG. 5, an exemplary embodiment of a sensor 200 is shown. The sensor 200 may include a control ring oscillator 210 and an exposed ring oscillator 240. The control ring oscillator 210 and the exposed ring oscillator 240 may be substantially similar and are essentially the same circuit as the ring oscillator 220, with one difference. The sensor 200 may be fabricated on a first semiconductor. The control ring oscillator 210 described above may include a first base substrate 202 and the resistors $r1-r_n$ may be protected from an environment by a first dielectric 208. The exposed ring oscillator 240 may include the first base substrate 202 while the resistors $r1-r_n$ may be exposed to the environment.

In an embodiment, the resistance change in carbon based sensors is converted to the frequency change of silicon based ring oscillator, then either transmits this frequency signal or stores it locally. Both graphene and carbon nanotubes to some extent behave as voltage controlled resistors. FIG. 1a shows a resistance curve of graphene as a function of gate voltage. It can be seen that the resistance is not constant. When it is contacted by some foreign material, its resistance curve shifts, as illustrated in FIG. 1.

In an embodiment, the ring oscillator 220 and the sensor 200 may be fabricated on a silicon substrate using existing fabrication techniques. The ring oscillator 220, made, for example, from CMOS inverters, is first made in the conventional manner, but instead of connecting the inverters with metal wires, the inverters are not connected and a space is left between them to make room for the environmental sensors. The graphene or carbon nanotubes form the resistors $r1-r_n$ which are wired or connected to the inverters $v1-v_n$. The graphene or carbon nanotube is left exposed to the atmosphere.

The effect of the resistance property difference in graphene or carbon nanotubes when sensitized to absorb a specific analyte may be used in this sensor, in the resistors $r1-r_n$. In the absence of the specific analyte, control ring oscillator 210 and the exposed ring oscillator 240 may have essentially the same frequency at the output B of each oscillator. In the presence of the specific analyte, control ring oscillator 210 and the exposed ring oscillator 240 may have a different frequency at the output B of each oscillator. The environmental sensing of the specific analyte may be thus converted to an electronic measurable signal.

In an embodiment, the sensor 200 may include one or more ring oscillators 220. Each of the ring oscillators 220 may include resistors $r1-r_n$ made of graphene or carbon nanotubes which have surface functionalization such that they are each sensitized to absorb a different analyte. Continuing in this embodiment, the control ring oscillator 210 may be included in the sensor 200. Alternatively, data including a ring oscillator 220 frequency in the absence of an analyte may be used as a benchmark to compare the ring oscillator 220 frequency to indicate possible environmental presence of an analyte for the ring oscillator 220.

In an embodiment, a frequency of the ring oscillator 220 is measured and stored or transmitted while in an environment free of the analyte. The ring oscillator 220 may then be placed in a new environment for the purpose of sensing the analyte. A new frequency of the ring oscillator 220 is measured in the environment and this new frequency is stored or transmitted. These two different measurements are compared to determine the presence of the analyte in the new environment.

In an embodiment, a frequency of the control ring oscillator 210 is measured and a frequency of the ring oscillator 220 is measured. These two different measurements are compared to determine the presence of an analyte in the environment.

Figure 6:
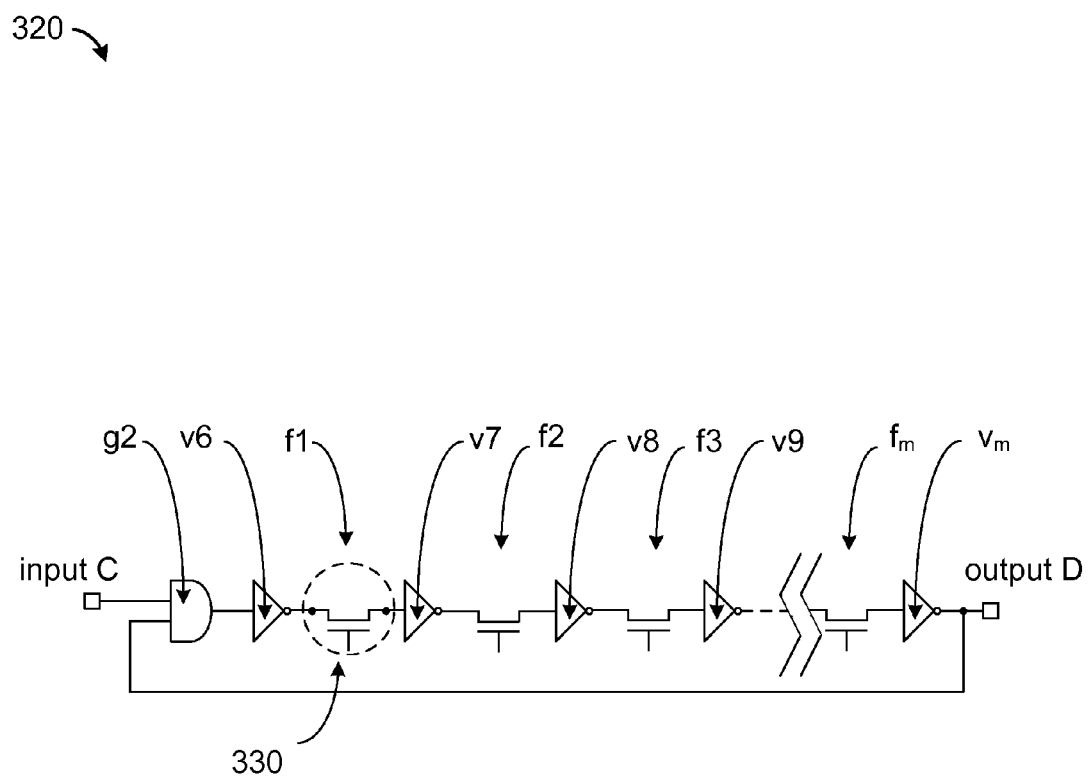
FIG. 6 is an electrical circuit diagram of an oscillator according to another exemplary embodiment.

Referring now to FIG. 6, an electrical circuit of an embodiment of a second ring oscillator 320 is shown, according to an exemplary embodiment. The second ring oscillator 320 may include an input C, an output D, an AND gate g2, inverters v6, v7, v8, v9, . . . $v_m$ and field effect transistors (hereinafter "FET") f1, f2, f3, . . . $f_m$ (hereinafter "FET"). The inverters v6, v7, v8, v9, . . . $v_m$ are connected in series, and the FETs f1, f2, f3, . . . $f_m$ are electrically connected between the inverters v6, v7, v8, v9, . . . $v_m$. The AND gate g2 has inputs of the input C and an output of the last inverter in the series, $v_m$. The output of the last inverter, inverter $v_m$, in the series of the inverters v6, v7, v8, v9, . . . $v_m$. is also output B. The FETs f1, f2, f, . . . $f_m$ may each have a gate channel which includes or carbon nanotubes.

The second ring oscillator 320 may perform in essentially the same manner as described above for the ring oscillator 220. It should be noted that, while the embodiment depicted in the figures may include one AND gate g2, five inverters v6-$v_m$ and four FETs f1-$f_m$, any number of FETs and an odd number of inverters may be used.

Figure 7:
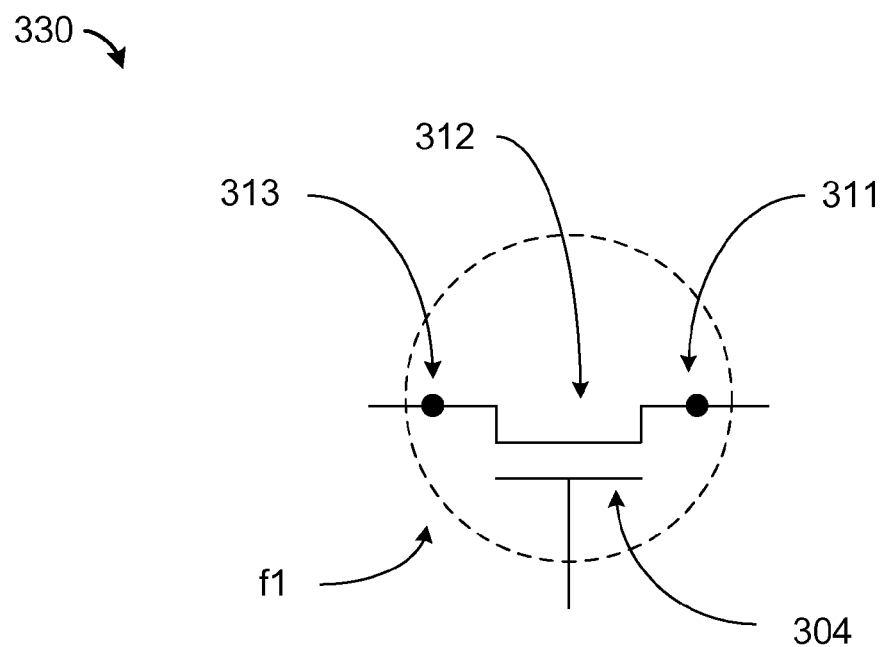
FIG. 7 is an electrical circuit diagram of a field effect transistor according to an exemplary embodiment.
Figure 8:
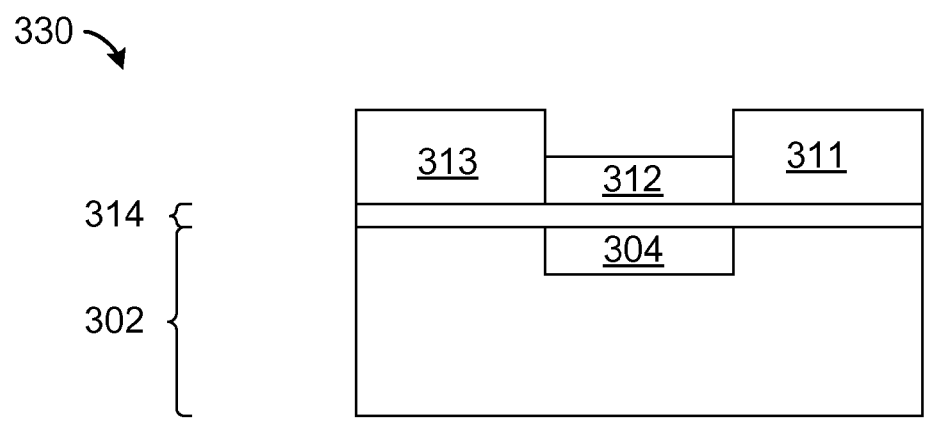
FIG. 8 is a vertical cross-sectional view of a semiconductor structure according to another exemplary embodiment.

Referring now to FIGS. 7 and 8, FIG. 7 is an embodiment of an electrical circuit diagram of the FET f1, while FIG. 8 is an embodiment of a semiconductor cross sectional view of the FET f1. FIG. 7 is a sectional view 330 of FIG. 6. The FET f1 may include a source 313, a drain 311, a gate 304, a gate dielectric 314 and a gate channel 312. The FET f1 may be fabricated on a second base substrate 302. In an embodiment, the gate channel 312 includes graphene or carbon nanotubes. The input C can turn the oscillation on or off.

The second base substrate 302 may be made from or formed from any of several known semiconductor materials such as, for example, a bulk silicon substrate. Other non-limiting examples include silicon, germanium, silicon-germanium alloy, silicon carbide, silicon-germanium carbide alloy, and compound (e.g. III-V and II-VI) semiconductor materials. Non-limiting examples of compound semiconductor materials include gallium arsenide, indium arsenide, and indium phosphide. Typically the second base substrate 302 may be approximately, but is not limited to, several hundred microns thick. For example, the second base substrate 302 may include a thickness ranging from 0.5 mm to about 1.5 mm.

Figure 9:
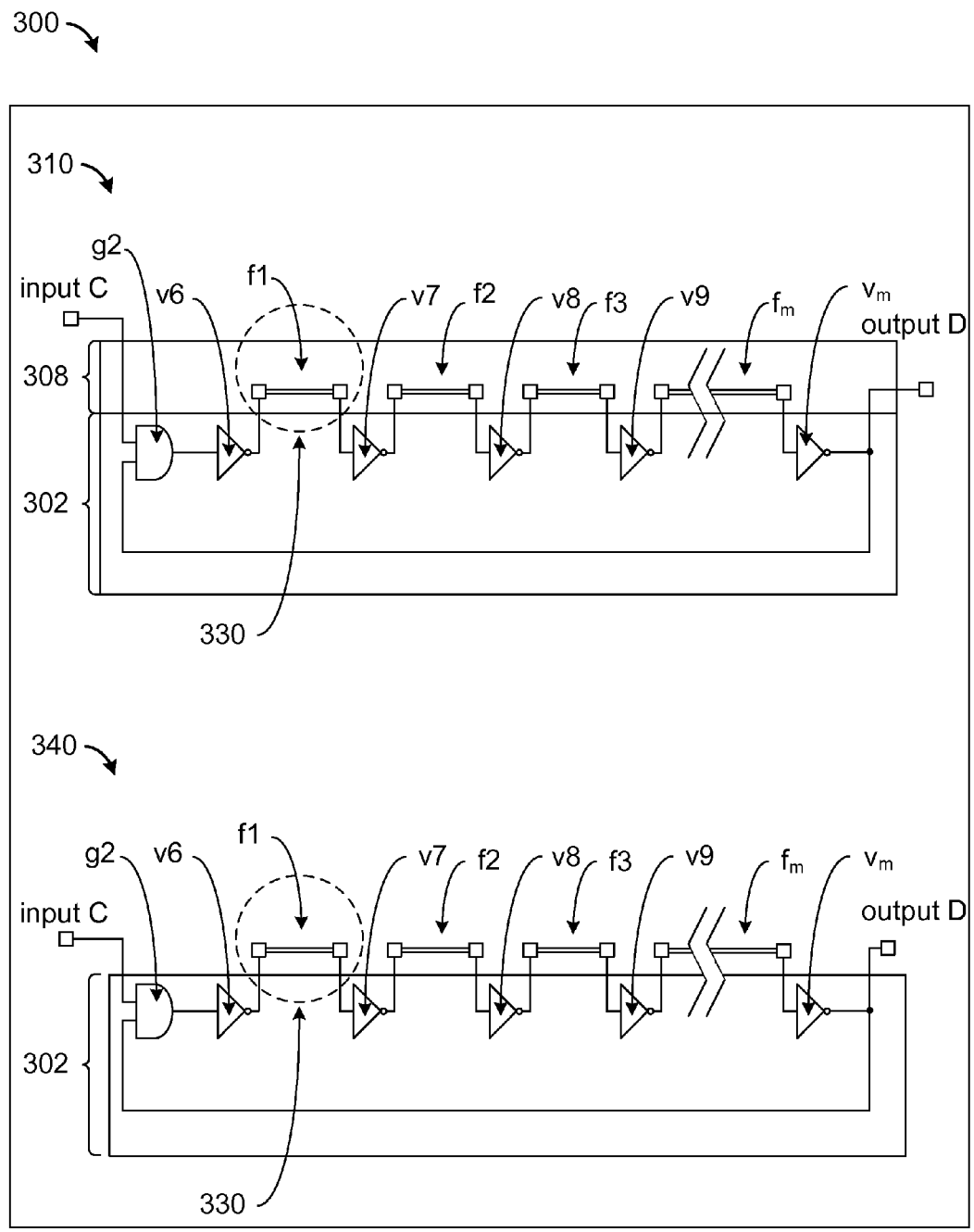
FIG. 9 is a view of a sensor according to another exemplary embodiment.

Referring now to FIG. 9, an embodiment of a second sensor 300 is shown. The second sensor 300 may include a control FET ring oscillator 310 and an exposed FET ring oscillator 340. The second sensor 300 may be fabricated on a second semiconductor. The control FET ring oscillator 310 and the exposed FET ring oscillator 340 are essentially may be substantially similar and are essentially the same circuit as described above for second ring oscillator 320, with one difference. The second sensor 300 may be fabricated on the second semiconductor. The control FET ring oscillator 310 described above may include a second base substrate 302 and the FETs f1, f2, f3, . . . $f_m$ may be protected by an environment by a second dielectric 308. The exposed FET ring oscillator 340 may include the second base substrate 302 while FETs f1, f2, f3, . . . $f_m$ may be exposed to the environment.

In this embodiment, the gate 304 is below the graphene or nanotube. The gate 304 can control the resistance of the FET f1 and the second ring oscillator 320. In the first ring oscillator 220, with a resistor structure, there is no gate and the resistance is determined by the material and the electrical properties resulting from its fabrication.

In an embodiment, the second ring oscillator 320 and the second sensor 300 may be formed or fabricated on a silicon substrate using existing fabrication techniques. The second ring oscillator 320, as described above, may be fabricated with CMOS FETs. Multiple metal levels may be constructed above the CMOS FETs using conventional back-end-of-line processes. Two metal levels may be connected by a via. After the gate 304 is formed, a thin gate dielectric may be deposited. A carbon device may then be deposited on top of the thin gate dielectric. The active region may defined by standard photolithography and etching, such as oxygen plasma. Finally, the contact metal to the carbon device, such as graphene or carbon nanotubes, may be deposited. The carbon device may be carbon engineered to have a sensitivity to a known analyte. The carbon device may be exposed to the atmosphere. In addition to the CMOS inverters, a gate electrode may be fabricated below the carbon device. The structure may operate as a voltage controlled oscillator, the voltage controlled oscillator may be controlled by controlling the gate 304 voltage.

In an embodiment, the second sensor 300 may include one or more second ring oscillators 320. Each of the second ring oscillators 320 may include a gate channel 312 made of graphene or carbon nanotubes which have surface functionalization such that they are each sensitized to absorb a different analyte. Continuing in this embodiment, the control FET ring oscillator 310 may be included in the second sensor 300. Alternatively, data may include second ring oscillator 320 frequency in the absence of an analyte may be used as a benchmark to compare the second ring oscillator 320 frequency to indicate possible environmental presence of an analyte for the second ring oscillator 320.

In an embodiment, a frequency of the second ring oscillator 320 is measured and stored or transmitted while in an environment free of the analyte. The second ring oscillator 320 may then be placed in a new environment for the purpose of sensing the analyte. A new frequency of the ring oscillator 320 is measured in the environment and this new frequency is stored or transmitted. These two different measurements are compared to determine the presence of the analyte in the new environment.

In an embodiment, a frequency of the control FET ring oscillator 310 is measured and a frequency of the second ring oscillator 320 is measured. These two different measurements are compared to determine the presence of an analyte in the environment.

In an embodiment, a method of sensing analytes including fabrication of a ring oscillator based on CMOS technology may include graphene or carbon nanotubes on fabricated silicon CMOS wafers. The absorption of analytes will change the conductance of the graphene or carbon nanotubes device, thus changing the ring oscillator frequency, making a transducer which produces a convenient electrical signal when an analyte is present.

Sensing of chemical and biological elements in the environment is important for environmental monitoring and security concerns. It is desirable to have sensors with high sensitivity to such elements, and also to transmit the sensed information remotely, by wired or wireless means, to a distant monitoring point. A frequency change can be easily transmitted to a remote detector.

It may be noted that not all advantages of the present invention are include above.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method of forming a sensor comprising:
    forming a ring oscillator on a semiconductor substrate, the ring oscillator comprises an AND gate, an odd number of inverters, and at least one carbon device, each carbon device being connected in series between two of the inverters, wherein the at least one carbon device is exposed to an analyte in an environment;
    forming a control ring oscillator on the semiconductor substrate, the control ring oscillator comprises an AND gate, an odd number of inverters, and at least one carbon device, each carbon device being connected in series between two inverters; and
    protecting the control ring oscillator from the environment.

2. The method of claim 1, wherein the carbon device comprises carbon engineered sensitivity to a known analyte.

3. The method of claim 1, wherein the carbon device comprises at least one of carbon nanotubes or graphene.

4. The method of claim 1, wherein the carbon device comprises a resistor.

5. The method of claim 1, wherein the carbon device comprises a field effect transistor, in which a channel of the field effect transistor comprises carbon.

6. The method of claim 1, wherein a multi-analyte sensor consists of a plurality of sensors, each of the plurality of sensors comprises a sensitivity to a different analyte.

7. A structure comprising:
    a ring oscillator on a semiconductor substrate, the ring oscillator comprising an AND gate, an odd number of inverters, and at least one carbon device, each carbon device being connected in series between two inverters, the carbon device being exposed to an environment such that a frequency of the ring oscillator changes when the carbon device is exposed to an analyte in the environment;
    a control ring oscillator on the semiconductor substrate, the control ring oscillator comprising an AND gate, an odd number of inverters, and at least one carbon device, each carbon device being connected in series between two inverters, each carbon device of the control ring oscillator being protected from the environment.

8. The method of claim 7, wherein the carbon device comprises carbon engineered sensitivity to a known analyte.

9. The structure of claim 7, wherein the wherein the carbon device comprises at least one of carbon nanotubes or graphene.

10. The structure of claim 7, wherein the carbon device comprises a resistor.

11. The structure of claim 7, wherein the carbon device comprises a field effect transistor, in which a channel of the field effect transistor comprises carbon.

12. A method of sensing an analyte in an environment comprising:
measuring a frequency of a ring oscillator on a semiconductor substrate, wherein the ring oscillator comprises an AND gate, an odd number of inverters, and at least one carbon device, each carbon device being connected in series between two inverters, wherein the frequency of the ring oscillator changes when the carbon device is exposed to the analyte in the environment; and
measuring a control frequency of a control ring oscillator on the semiconductor substrate, wherein the control ring oscillator comprises an AND gate, an odd number of inverters, and at least one graphene device, each graphene device being connected in series between two inverters, the graphene device being protected from the environment.

13. The method of claim 12, further comprising:
determining the presence of an analyte in the environment by comparing the measured frequency of the ring oscillator to a control frequency.

14. The method of claim 12, further comprising transmitting or storing the frequency of the ring oscillator.

15. The method of claim 12, further comprising:
determining the presence of the analyte in the environment by comparing the measured frequency of the ring oscillator to the measured control frequency of the control ring oscillator.

16. The method of claim 12, further comprising engineering the sensitivity of a carbon device to the known analyte.

17. The method of claim 12, wherein the method further comprises fabricating the carbon device as at least one of a resistor, and a field effect transistor.

* * * * *